United States Patent [19]

Albanese

[11] Patent Number: 4,904,464

[45] Date of Patent: * Feb. 27, 1990

[54] INSECTICIDE AND AIR FRESHENER PREPARATIONS

[75] Inventor: James J. Albanese, Eureka, Mo.

[73] Assignee: United Industries Corporation, St. Louis, Mo.

[*] Notice: The portion of the term of this patent subsequent to Mar. 27, 2001 has been disclaimed.

[21] Appl. No.: 237,372

[22] Filed: Aug. 29, 1988

Related U.S. Application Data

[60] Division of Ser. No. 708,091, Mar. 4, 1985, Pat. No. 4,826,674, which is a continuation of Ser. No. 648,629, Sep. 10, 1984, abandoned, which is a continuation of Ser. No. 410,375, Aug. 23, 1982, abandoned.

[51] Int. Cl.$^4$ .................... A01N 25/00; A01N 65/00; A01N 57/00
[52] U.S. Cl. ................. 424/45; 424/DIG. 11; 514/65; 514/75; 514/122; 252/305; 252/312
[58] Field of Search .................... 514/45, 65, 75, 122; 424/DIG. 11; 252/312, 522, 305

[56] References Cited

U.S. PATENT DOCUMENTS 4,439,344 8/1988 Albanese ........................... 252/312

Primary Examiner—John W. Rollins
Attorney, Agent, or Firm—Kalish & Gilster

[57] ABSTRACT

An insecticide preparation which may be either aerosolized or non-aerosolized is in the form of a dispersion with normally distinct sharply delineated water and active ingredient phases. The preparation contains a dispersal agent consisting of cocodiethanolamide within the range of 0.1 to 10% by weight of the preparation and with the preparation having a pH within the neutral range of approximately 6.5 to 7.5.

12 Claims, No Drawings

INSECTICIDE AND AIR FRESHENER PREPARATIONS

This is a division of application Ser. No. 708,091 filed Mar. 4, 1985, now U.S. Pat. No. 4,826,674 which is a continuation of application Ser. No. 648,629 filed Sept. 10, 1984 now abandoned, which is a continuation of application Ser. No. 410,375 filed Aug. 23, 1982 now abandoned.

BACKGROUND AND SUMMARY OF THE INVENTION

This invention relates in general to chemical compositions and, more particularly, to insecticides and air fresheners which are so uniquely formulated that marked economies in production are effected, and previously recognized potential hazards are eliminated.

Heretofore, insecticidal preparations, both aerosolized and non-aerosolized, have customarily and expectedly embodied ingredients inherently dangerous to the user, as therein a solvent serves as the carrier. The same have been potentially harmful for a variety of reasons, including, among others, possible flammability, as with petroleum distillates, isopropanol, acetone, aromatic solvents, such as, xylene, etc.; or an inherent hazard for damaging surfaces, such as, floors, furniture, and the like upon which such preparations might ultimately come to rest, as illustratively wherein methylene chloride, to mention one of the most common, would serve as the carrier; or present a serious peril to the health of the user, with especial concern for disorders of the nervous system, with there being a veritable host of well known carriers capable of such activity. In addition to all such possible hazards through use of currently available insecticides, in aerosolized insecticides, wherein typically an emulsion has been formed, and with the carrier being water, considerable expense is entailed in providing the necessary degree of propellant. Similarly, with air freshener preparations, in aerosolized form, such as, room deodorizers, and the like, there is included necessarily an exceedingly high proportionality of propellant which renders such preparations relatively costly.

Consequently, it would be desired with aerosolized and non-aerosolized insecticides to reduce the level of the carrier which is the source of the dangers outlined, while also with aerosolized insecticides, as well as air fresheners which are already water based, the aim would be to lower costliness in production which could be achieved by reducing the relative amount of propellant. To the present time, as preferable as these goals might be, the same have not been accomplished.

However, by means of the present invention, it has been found that the incorporation within such preparations of cocodiethanolamide, as developed hereinbelow, quite unexpectedly and surprisingly produces the results sought with respect to the insecticides and air fresheners by reason of the unique property of serving as a dispersal agent. This unusual property of cocodiethanolamide has been disclosed in applicant's co-pending applications Ser. Nos. 282,050 now U.S. Pat. No. 4,439,343 and 237,155, now U.S. Pat. No. 4,439,342 entitled "Aerosol Preparations", as well as in bulk form in pending application Ser. No. 250,745, now U.S. Pat. No. 4,439,344 entitled "Water Dispersions". Thus, it is to be understood that with the present invention cocodiethanolamide is not incorporated for utilization of its recognized emulsifying and stabilizing properties, but is used to bring about, within the systems of the preparations of the type stated, a condition tantamount to an unstable emulsion wherein the phases tend to separate, but are transitorily intermixed into relative stability upon agitation. Upon dispensing immediately subsequent to the agitation, the phases will separate and revert to the constituent components. Thus, with the present invention, without any intention of limitation, the preparations will be referred to as dispersions to signify the inherent instability, as distinguished from emulsions with which cocodiethanolamide has been historically associated. As disclosed in applicant's aforesaid co-pending applications, the dispersion characteristics of the preparation are controlling, as distinguished from the expected emulsion characteristics of the dispensed preparations.

Therefore, it is an object of the present invention to provide insecticide preparations, both aerosolized and non-aerosolized, and aerosolized air fresheners which embody a dispersal agent whose presence eliminates the heretofore reluctantly accepted hazards presented by the commonly used solvents for the particular active ingredients.

It is another object of the present invention to provide insecticides and air fresheners in aerosol form which embody an amount of propellant markedly reduced from that currently considered requisite for effective dispensation.

It is a further object of the present invention to provide insecticidal and air freshener preparations which may incorporate as active ingredients liquids and combinations of liquids, as well as powders.

It is a still further object of the present invention to provide insecticide preparations, both in aerosolized and non-aerosolized form, and aerosolized air fresheners which permit utilization of water as a carrier for hydrophobic chemicals, as well as for chemicals that have been previously delivered by means of petrochemical, or other non-aqueous solvents; and, additionally, for improving the effectiveness of current systems which may incorporate water as a carrier.

It is another object of the present invention to provide an insecticidal preparation which embodies a dispersal agent for elimination of the usual potential hazards without diminution in the biological activity of the agent or agents being dispensed since such preparations may incorporate various combinations of ingredients to endow the preparation with the designed insect-treating qualities, such as, residual action alone, or with repellancy, knock-down, etc.

It is a further object of the present invention to provide a preparation of the character stated wherein the physical and chemical characteristics of the active ingredients are unaltered from the pre-diluted state thereof.

It is another object of the present invention to provide preparations of the character stated which possess substantially indefinite shelf life so that regardless of the transpired interval between production and dispensing, no loss of activity occurs.

It is a still further object of the present invention to provide preparations of the character stated which may be economically produced in accordance with well known production techniques so that novel instrumentation and equipment are not required.

DESCRIPTION OF THE INVENTION

The present invention contemplates the development of insecticide preparations, both aerosolized and nonaerosolized, and aerosolized air fresheners, which, by reason of the incorporation of cocodiethanolamide in a manner to serve as a dispersal agent, are physically and chemically distinct from classical stable emulsions.

The system of the present invention embodies generally immisicible phases, one being a water phase, and the other being a continuous phase; which phases are clearly defined, being sharply distinct with a clear line of delineation. The active ingredient for the purposes of this invention is primarily in the continuous phase which might be considered the "oil" phase, which phase contains the aforesaid dispersal agent; the same being soluble in both phases, but to different degrees. Thus, preparations of the present invention in their normal tranquil state will be unhomogenized, with the definition between the two phases being visibly unmistakable. Thus, preparations of the type herein disclosed are not stable emulsions, but, as expressed above, are referred to as "dispersions" for purposes of exposition. But in addition to entailing the dispersal agent, the two phase systems of the present invention possess a controlled pH which may be described as being "substantially neutral", that is, within the range of approximately 6.5 to 7.5. This particular condition is one of critical importance.

The necessity for maintaining a pH within the aforesaid neutral range is not entirely understood; but it is believed that with a pH in the alkaline range, that is, above approximately 7.5, the cocodiethanolamide which when dispersed in water possesses an inherent pH of about 9, will function in its normally expected manner, that is, as a soap, emulsifier, or stabilizer, and that when cocodiethanolamide is within an acid environment, that is, below approximately 6.5, the acid constituents of cocodiethanolamide are free to react in a manner consistent with acids. Therefore, the development of pH in the aforesaid neutral range with the preparations of the present invention in some manner uniquely enables the contained cocodiethanolamide to act as a dispersal agent and, thus, in a fashion quite unexpected in light of its generally known properties. Furthermore, it has been discovered that these formulations are of maximum effectiveness, with the pH thereof in the neutral range, that is, by providing the proper particle size, the degree of biological activity, etc.

Typically with all the myriad insecticide preparations and air fresheners studied and analyzed, the same are formed with a pH slightly on the alkaline side, since the pH of a 1.0% water dispersion of cocodiethanolamide-*is approximately 9.0. It is, of course, understood that other factors than the pH of the cocodiethanolamide might, to some extent, dictate the inherent pH as by reason of the fundamental acidity or alkalinity of certain active ingredients. Although, as indicated, it appears that all insecticide active ingredients are water insoluble so that there would be no inherent pH and, accordingly, the control of the inherent pH by the cocodiethanolamide would be apparent. Those particular active ingredients for insecticides and air fresheners which possess some tendency to hydrolyze appear to uniformly provide an alkaline pH. Consequently, to all intents and purposes, the pH of the cocodiethanolamide would be the pH controlling entity within the systems herein considered. Thus, with the pH above the neutral range, the adjustment thereof is accomplished in the ordinary fashion, that is, by utilization of acidic agents, such as, dilute acid solutions, including, for example only, dilute nitric acid, dilute phosphoric acid, dilute citric acid, ad infinitum. In accordance with commonly practiced techniques, the selection of the particular acidic agent is grounded upon its non-reactiveness with other chemicals in the system so as not to produce unwanted compounds that might in some way adversely affect the ultimate product, that is, either chemical stability, container stability, etc. Merely exemplary would be the fact that dilute citric acid would not be an acidic agent of choice for aerosols since it might cause the formation of citrates which have a corrosive effect upon the particular containers. The selection of the appropriate acidic agent does not exceed the capacity of chemists having ordinary skill in the art.

*A preparation of this compound which is fully effective for the purpose of this invention constitutes an amber liquid having a congealing point of approximately 6° C. and with a specific gravity at 25° C. of 0.99. The free or unreacted fatty acid, as lauric, 3%-4% maximum and the pH 1% dispersion is between 8 and 9. This compound is stated to possess solubility in alcohols, glycols, ketones, esters, aromatic and aliphatic hydrocarbons and chlorinated solvents, while also being dispersible in water at low concentrations of 1 to 2%. It is stated to become soluble at higher concentrations and with a 10% solution being quite viscous approximating a gel. Such preparation is commercially offered under the trademark CLINDROL 101-CG by Clintwood Company, Chicago, Ill.

The adjusting of the insecticide and air fresheners of the present invention can manifestly be accomplished in various ways; the most facile being to adjust the inherent pH, such as, 9.0, after the dispersion has been formed with the included active ingredients and the like. However, adjusting can also be achieved by adding the dilute acid solutions directly to the water after it has been determined experimentally precisely that amount of chemicals required to attain the neutral range. This last-mentioned method has particular advantages where the water is added in an aerosol as a separate filling stage. As indicated, the development of the resultant pH is brought about in the usual manner, that is, by adding a predetermined amount to the dispersion, then mixing the dispersion by the use of standard mixing equipment for a preselected period, and then determining the pH, with additional acidic agent being added as indicated.

The importance of the neutral range of the preparations of the present invention has been well demonstrated by the fact that with aerosol preparations a pH outside of such range, on either side, has a direct and immediate affect upon the particle size causing the same to be relatively too large or to take on an undesired foam-like characteristic. Also, failure to observe the aforesaid neutral range is productive of a grave diminution in the biological activity of an insecticide. With air fresheners, elevated particle sizes or foam will cause droplets of undesired volume to deposit upon adjacent surfaces, such as, furniture, flooring, walls and the like, with deleterious affect thereon, as well as to cause the air freshener to have a loss in effective capacity to accomplish its intended purpose.

Thus, the adjusting above discussed is a requisite step since the inherent pH is substantially controlled by the dispersal agent and, with the adjusting to the critical neutral range, no chemical alteration of the ingredients is effected so that the properties thereof are unaffected.

The relative amount of cocodiethanolamide to serve as a dispersal agent for the present preparations has been found that for either aerosolized or non-aerosolized preparations the same will fall within a range of approximately 0.1% to 10% of the weight of the ultimate preparation so that extremely limited amounts are efficacious for the various applications. The relative amount of cocodiethanolamide to be used is determined by the particular spray characteristics sought which, of course, are dependent upon the particular end use of the preparation to be dispensed. It is apparent that particle size may be the determinant, such as, for example, in a space spray. Therefore, cocodiethanolamide is added in limited increments until the desired characteristics have been met. But, as a matter of extensive investigative experience, it has been found that with insecticide preparations and air fresheners, the cocodiethanolamide will fall within a range of 0.1% to 1.0% of the weight of the preparation or may necessitate up to approximately 2.4%, whether the system be aerosolized or not. As more fully developed hereinbelow, a relatively small quantity of cocodiethanolamide, together with the provision of a pH within the aforesaid neutral range, will permit of such relative reduction in the amounts of solvents for the active ingredients as to substantially eliminate the hazards normally presented by such solvents. The preparations wherein a significant portion of the carrier has been a solvent the relative quantity of the carriers for preparations of the present invention are in the general order of but 5.0% of that which has been heretofore deemed necessary for compositions of such character, and being replaced by water. It is understood that in certain compositions there may be some limited variance from 5.0%. In addition to rendering such preparations effectively free of hazardous contingencies, substantial economies may obviously be effected in production since water is substituted for the unnecessary costly carriers. As indicated, the active ingredients of insecticide preparations, such as, for example, carbamates, organo-phosphates, and the like, have required solvents serving as the carrier which present a high danger potential in one form or another. Among the more common carriers, petroleum distillates, acetone, isopropanol, butyl Cellosolve*, various aromatic solvents, such as, xylene, toluene, etc., are flammable; while others, such as, methylene chloride, present a health hazard as well as being productive of damaging effects upon spray-receiving surfaces. The foregoing is not intended to be comprehensive, but merely indicative of the general character of carriers heretofore utilized in insecticides which are of a recognized perilous potential. ≠*Trandemark of Union Carbide Corp. for ethylene glycol monobutyl ether.

Furthermore, with aerosolized preparations wherein water is already utilized as a carrier, the present invention will permit the reduction of the relative quantity of the propellant, with consequent commensurate increase in the amount of water and thus bring about a consieerable monetary saving.

Active ingredients for incorporation in insecticide preparations according to the present invention, whether aerosolized or otherwise, are substantially water insoluble and comprehend the myriad compounds having the known desired characteristics. The following are to be considered merely exemplary since it is within the capacity of one having ordinary skill in this art to make the selection of the active ingredient.

One such group consists of the natural and synthetic pyrethrins or pyrethroids, which latter are considered "mimics" of the natural pyrethrins in that they possess comparable properties, but diverge markedly in chemical structure. Among such synthetics may be found sumethrin, resmethrin, tetramethrin, permathrin, d-trans allethrin,

*Trademark of Union Carbide Corp. for ethylene glycol monobutyl ether. allethrin, fenvalerate, and phenothrin. Used in combination with the pyrethroids both natural and synthetic, is a class of compounds considered as synergists and include, among others, piperonyl butoxide, n-octyl-bicycloheptene dicarboximide, butoxy polypropylene glycol, and 2-hydroxyethyl-n-octyl sulfide.

Another major group of insecticides are the carbamates, smong the better known of which are propoxyur, 1-naphthyl n-methyl carbamate, Ficam*, etc. ≠*A trademard of BFRC Chemical Co. of Wilmington, Delaware for 2,2-dimethyl-1,3-benzodioxol-4-ol methyl carbamate An additional group of well known insecticides comprises the organo-phosphates, among which are diazinon, chlorpyrofos, dimethyl dichlorovinyl phosphate (DDVP), etc.

Accordingly, the foregoing is not intended to be an exhaustive enumeration of the various active ingredients for insecticides of the present invention, but merely serves to indicate that effectively all generally known insecticidal active ingredients are adaptable for incorporation.

With respect to aerosol preparations, the propellants utilized are of generally accepted types, that is, liquefied, such as, hydrocarbons or halocarbons, and blends of the same, or compressed gases, or combinations of liquefied and compressed gases. The selection of the propellant is dependent upon desired characteristics relative to evaporation rate, solubility, pressure, as well as economics and safety, all in accordance with present day considerations. It is to be undersood that the choice of propellant in the present invention is dictated by the same considerations as in aerosol preparations generally
*A trademark of BFC Chemical Co. of Wilmington, Delaware for 2,2-dimethyl-1,3-benzodioxol-4-ol methyl carbamate and, thus, the precise propellant does not form a part of the present invention.

In order to control the properties of the selected propellant, an organic auxiliary solvent may be selected from a very wide range, all as in accordance with known technology. Such solvents are for film controlling purposes to assure that a foam is not created, as well as for controlling the evaporation rate, which latter may also be controlled by selecting a combination of solvents that will dry in unison with the active ingredients. With the insecticides of the present invention in aerosolized form, it is not of immediate significance whether a film is formed, the criterion being that the dispersed material possesses the desired particle size, effective biological activity and the like. Wherefore, foam formation is undesired so that in the present context the term "film controller" is used primarily to signify an agent inhibiting foam formation just as the compounds referred to as auxiliary solvets. "Organic auxiliary solvents" and "film controllers" are interchangeable terms herein.

Included among such solvents are those which have heretofore been widely known in the aerosol field, such as, aromatic hydrocarbons, examples of which are benzene, toluene, xylene, commercial solvents which flash at 100° and 150° ; aliphatics, and aliphatic petroleum napthas, such as heptane, hexane, kerosene, lacquer diluent, napthol spirits, mineral seal oil, mineral spirits, odorless mineral spirits, deodorized kerosene, pentane, petroleum ether, Stoddard solvent, textile spirits, VM&P naptha, isoparaffinic hydrocarbons, petroleum distillates, as well as mixtures and blends thereof.

Another general class of auxiliary solvents or film controllers are the chlorinated hydrocarbons; among the more commonly used are carbon tetrachloride; 1,1,1-trichlorethane, methylene chloride, and perchlorethylene.

Among other agents suitable for controlling the propellant are mineral oils with boiling points above 300° F. including white oils, such as DRAKEOL* #7, paraffinic oils, and isoparaffinic oils; including glycols with initial boiling points above 350° F., such as propylene glycol, ethylene glycol, hexylene glycol, dipropylene glycol, diethylene glycol and triethylene glycol; including glycol ethers with initial boiling points above 350° F., such as dipropylene glycol monomethyl ether, diethylene glycol monoethyl ether, diethylene glycol monomethyl ether, diethylene glycol monobutyl ether and tripropylene glycol monoethyl ether; and including aromatic blends or composition solvents containing a high content of aromatic hydrocarbons with initial boiling points above 360° F., such as HI-SOL 15**.

A trademark of Pennreco, Inc. to identify a series of white mineral oils, colorless, odorless and tasteles hydrocarbon distillates meeting the U.S.P. XV and N.F.X requirements for "petroleum liquidum".
**A trademark of Ashland Chemical Company for aromatic petroleum solvents.

The active ingredient may not be entirely soluble in the particular solvent or film controller utilized but a low degree of solubility does permit of the solvent or film controller as forming a bridge, as it were, between the active ingredient and the propellant having a solubilizing, even though limited, effect thereupon. A limited amount of such agent, as within the range of 2% to 5% by weight is sufficient and is manifestly applicable where the propellant is liquefied.

In addition to the foregoing, which is not meant to suggest an exhaustive compilation of suitable auxiliary solvents, there may be included tetra hydrofuran and 2-nitropropane. As indicated above, and as is implicit in the involved chemistry, the choice of solvent is made in accordance with well known considerations, such as, as indicated, evaporation rate control, compatibility with the particular active ingredient, etc. Further, it is understood that such solvents may be intermixed or blended to produce a desired resultant characteristic. The blending of heptane and hexane is but illustrative in that a blend of the same would dry somewhat slower than hexane alone, but faster than heptane if used alone.

The choice of auxiliary solvent is dictated by the same general considerations as in the field of aerosols and, hence, the precise auxiliary solvent does not form a part of the present invention.

In the production of insecticide preparations in accordance with the present invention, the relative quantity of the insecticidal active ingredient is determined in accordance with generally accepted, customary practice. Thus, from currently available literature the amounts of recognized insecticidal agents to kill insects of various types can be readily obtained. Thus, for example, with insects of the flying type, 0.1% pyrethrins may be lethal; with insects of the crawling type a greater amount of the agent would be required, such as, in the order of 0.3%. In those situations wherein the available literature does not provide definitive information on this particular point, the amount necessary can be experimentally determined by biological assays, all in accordance with well known laboratory techniques.

The present invention does not alter the relative amounts of insecticidal agents incorporated than had been heretofore required since such are determined by the same parameters, namely that level of biological activity requisite to achieve the desired results upon the particular insect or type of insect forming the target. It is recognized that with some agents 0.5% by weight of the particular preparation would be adequate so that herein it should be understood that the amount of insecticide agent will be within the range which has been either historically or experimentally observed as critical.

Thus, in essence, insecticidal preparations formed in accordance with the present invention comprise three basic constituents namely the insecticide active ingredient or combinations thereof which will be in a quantity sufficient (q.s.) for the particular application in accordance with the foregoing; cocodiethanolamide within a range of 0.1% to 10% by weight of the preparation; with the balance being water, which could be as much as 99.85%, as wherein the cocodiethanolamide would represent 0.1% and the insecticide 0.05% by weight. To achieve certain specific desired effects there may be added various solvents and other ingredients to the preparation, at the expense of the water; reference, for example, being made to agents for affecting viscosity, particle size, odor, and the like. The foregoing would be applicable to preparations which were non-aerosolized.

However, to render the insecticide preparation in aerosol form, a relatively small percent of solvent is further added to aid in incorporating the propellant within the system when such propellant is a liquefied compressed gas; such additional solvent or film controlling agent being generally within the range of approximately 2.0 to 5.0% by weight which has been found normally sufficient; although 1% to 20% would be satisfactory. This additional solvent will proportionately reduce the water content. With compressed gases alone no solvent may be necessary, but it could range up to 20% depending upon the spray characteristics desired. The particular propellant selected, that is, whether a compressed gas or a liquefied compressed gas, or combination thereof, will be determined by the specific spray characteristics sought, all as may be more evident from the examples set forth hereinbelow. The propellant will, of course, cause a further reduction in the amount of water from that which would have been used in a non-aerosol or so-called bulk formulation as above outlined.

Aerosol insecticide preparations possessing the properties of the present invention have the following general formula wherein liquefied compressed gas propellants, namely the hydrocarbons and halocarbons, are used:

|  | PERCENT BY WEIGHT |
| --- | --- |
| Active Ingredient Dispersal Agent | q.s. |
| cocodiethanolamide | 0.1% to 10% |
| Solvent/Film Controlling Agent | Approx. 1% to 20% |
| Propellant | Approx. 2.5% to 30% |
| Water | Approx. 35% to 96.3% |

In those preparations wherein compressed gas constitutes the propellant, the general formulation would be as follows:

|  | PERCENT BY WEIGHT |
| --- | --- |
| Active Ingredient Dispersal Agent | q.s. |
| cocodiethanolamide | 0.1% to 10% |
| Solvent/Film Controlling Agent | Approx. 0% to 20% |

-continued

| | PERCENT BY WEIGHT |
|---|---|
| Propellant | Approx. 0.1% to 5% |
| Water | Approx. 35% to 99.5% |

In the insecticide preparation wherein the propellant comprises a combination of compressed gases and liquefied compressed gases, the general formula would be as follows:

| | PERCENT BY WEIGHT |
|---|---|
| Active Ingredient | q.s |
| Dispersal Agent | |
| cocodiethanolamide | 0.1% to 10% |
| Solvent/Film Controlling Agent | Approx. 1.0% to 20% |
| Propellant | |
| liquefied | Approx. 2.0% to 30% |
| gaseous | Approx. 0.1% to 5% |
| Water | Approx. 35% to 96.7% |

The application of these formulations will become more comprehensible from a study of specific formulae set forth hereinbelow. It is to be understood that preparations incorporating the below exemplary formulae are adjusted within the aforesaid neutral range of 6.5 to 7.5 as described hereinabove. Also the examples will demonstrate the versatility of the present invention for providing insecticides having various selected qualities, such as, repellancy, residual action, knock-down, sound reduction, etc.

INSECTICIDE AEROSOL PREPARATIONS

EXAMPLE I

| Flying Insect Spray | |
|---|---|
| | PERCENT BY WEIGHT |
| Pyrethrin (20% extract) | 2.5% |
| Technical Piperonyl Butoxide | 1.5% |
| Petroleum Distillate | 10.0% |
| Cocodiethanolamide | 0.5% |
| Water | 70.5% |
| (Isobutane 35%) | 15.0% |
| (Propane 65%) | |

The foregoing formulation demonstrates the use of a pyrethroid, more particularly, pyrethrin, as synergized by piperonyl butoxide and wherein the petroleum distillate is optionally incorporated for providing a predetermined spray characteristic, as is commonly practiced with insecticidal aerosol preparations; which, in this case, assists the propellant in providing a relatively far reaching spray, as well as serving to a very limited extent as a carrier. The propellant is a combination of liquefied hydrocarbons.

EXAMPLE II

| Wasp and Hornet Insect Spray | |
|---|---|
| | PERCENT BY WEIGHT |
| Resmethrin (40% Technical Concentrate) | 0.625% |
| Butyl Cellosolve | 2.5% |
| Cocodiethanolamide | 2.4% |
| Water | 93.975% |
| Nitrogen | 0.50% |

This particular preparation illustrates the embodying of an options thinning agent, such as, butyl Cellosolve, a well known expedient to those skilled in this field, which thus decreases surface tension and thereby increases the distance of propulsion of the spray, as well as serving in a most limited fashion as a carrier. The relatively substantial amount of water indicates clearly the advantage gained by the present invention in hazard reduction. A compressed gas, such as, nitrogen, is shown as the propellant.

EXAMPLE III

| Total Release Insect Fogger | |
|---|---|
| | PERCENT BY WEIGHT |
| D-trans allethrin (90% technical) | 0.333% |
| Sumethrin | 0.20% |
| Petroleum Distillate | 14.467% |
| Cocodiethanolamide | 2.4% |
| Water | 62.600% |
| (Isobutane 35%) | 20.0% |
| (Propane 65%) | |

In this formulation the insecticidal active ingredient is actually a combination of two such agents so as to provide the desired characteristics, such as, flushing, quick knock-down, and kill. The petroleum distillate acts partially as a solvent for the propellant and also as an aid in achieving desired particle size.

EXAMPLE IV

| Total Release Insect Fogger | |
|---|---|
| | PERCENT BY WEIGHT |
| Tetramethrin (90% technical) | .22% |
| Sumethrin | .20% |
| Petroleum Distillate | 4.00% |
| Cocodiethanolamide | .60% |
| Water | 74.98% |
| (Isobutane 65%) | 20.00% |
| (Propane 35%) | |

This formulation is basically similar to Example III above, with the petroleum distillate being heptane.

EXAMPLE V

| Flea and Tick Spray | |
|---|---|
| | PERCENT BY WEIGHT |
| Allethrin (90% technical) | 0.11% |
| Technical Piperonyl Butoxide | 1.0% |
| Butoxy Polypropylene Glycol | 5.0% |
| Butyl Cellosolve | 2.5% |
| Cocodiethanolamide | 1.0% |
| Water | 86.89% |
| Carbon Dioxide | 3.5% |

The foregoing formulation is an example of an aerosol insecticide wherein allethrin, a synthetic pyrethroid, is the insecticidal active ingredient and subjected to the synergistic agent piperonyl butoxide. Although butoxy polypropylene glycol possesses insecticidal properties, the same is incorporated in view of its repellant capacity. Butyl Cellosolve is fundamentally included for its surface tension decreasing property which promotes sound reduction in view of its operating with a propellant consisting of a compressed gas. With liquefied compressed gases as the propellants a hissing sound would normally be generated by the escape of the gas which would tend to alert the quarry.

EXAMPLE VI

| Residual Ant and Roach Spray with Repellants | |
|---|---|
| | PERCENT BY WEIGHT |
| Pyrethrins (20% technical) | 0.375% |
| Technical Piperonyl Butoxide | 0.150% |
| N—octyl bicycloheptene dicarboximide | 0.250% |
| 2-hydroxyethyl-n-octyl sulfide | 1.0% |
| Petoleum Distillate | 5.0% |
| Butyl Cellosolve | 2.4% |
| Cocodiethanolamide | 0.1% |
| Water | 85.525% |
| Dimethyl Ether | 5.0% |
| Nitrogen | 0.2% |

The foregoing formulation exemplifies a residual insecticide, aerosolized, wherein the active ingredient is a pyrethrin, which is synergized by the piperonyl butoxide. The n-octyl-bicycloheptene dicarboximide serves both to synergize the pyrethrin, as well as to co-ordinate with the 2-hydroxyethyl-n-octyl sulfide to provide a relative enhanced repellancy to the preparation. Petroleum distillate serves as a solvent, while the butyl Cellosolve promotes thinning.

EXAMPLE VII

| Residual Ant and Roach Killer With Quick Knock-Down | |
|---|---|
| | PERCENT BY WEIGHT |
| Propoxyur (96% technical) | 1.1% |
| DDVP (93% technical) | 0.54% |
| Isopropyl Alcohol | 8.00% |
| Methylene Chloride | 4.00% |
| Odorless Mineral Spirits | 10.00% |
| Cocodiethanolamide | 2.40% |
| Water | 63.96% |
| (Isobutane 50%) (Propane 50%) | 10.00% |

In this formulation, the active ingredient is, in fact, a combination of a carbamate and an organo-phosphate, with the former being in powder form. Thus, two solvents are incorporated in the isopropyl alcohol and methylene chloride. The odorless mineral spirits, a petroleum distillate, serves a dual function, namely to act as a solvent for the propellant, as well as to provide the preparation with increased spray projectivity.

EXAMPLE VIII

| Flea and Tick Spray with Repellant | |
|---|---|
| | PERCENT BY WEIGHT |
| Tetramethrin (90% technical) | 0.11% |
| Sumethrin | 0.10% |
| Wettable Sevin* (60% technical) | 0.83% |
| R-11 | 0.50% |
| Heptane | 2.00% |
| Cocodiethanolamide | 0.30% |
| Water | 81.16% |
| (Isobutane 50%) (Propane 50%) | 15.00% |

*A trademark of Union Carbide Corp. for 1-naphthyl n-methyl carbamate

With the foregoing formulation, the active ingredient comprehends three agents falling within the categories of carbamates and pyrethroids. R-11 is the identity for a commercial preparation which will provide repellancy.

It may be pointed out that this formulation could be rendered non-aerosolized by simply increasing the water by 15% by weight to a total of 96.16% and eliminatig the propellant.

EXAMPLE IX

| Flying Insect Spray | |
|---|---|
| | PERCENT BY WEIGHT |
| Resmethrin (40% technical) | 0.375% |
| D-trans allethrin (90% technical) | 0.110% |
| Petroleum Distillate | 2.500% |
| Cocodiethanolamide | 0.25% |
| Water | 81.765% |
| (Isobutane 50%) (Propane 50%) | 15.00% |

INSECTICIDE NON-AEROSOL PREPARATIONS

EXAMPLE X

| Residual Ant and Roach Killer | |
|---|---|
| | PERCENT BY WEIGHT |
| Dursban F* (94% technical) | 0.53% |
| Xylene | 0.33% |
| Cocodiethanolamide | 0.1% |
| Water | 99.04% |

*A trademark of Dow Chemical Company for O,O—diethyl (O—3,5,6-trichloro-2-pyridyl) phosphorothioate This preparation is exemplary of utilizing an active ingredient in powder form and with a solvent therefor, namely xylene in this instance, being in minimal quantity.

EXAMPLE XI

| Residual Ant and Roach Killer with Quick Knock-down | |
|---|---|
| | PERCENT BY WEIGHT |
| Dursban F (94% technical) | 0.53% |
| D-trans allethrin (90% technical) | 0.056% |
| Xylene | 0.33% |
| Cocodiethanolamide | 0.1% |
| Water | 98.984% |

This formulation, which is similar to that of Example X, demonstrates the inclusion of a further ingredient to endow the preparation with a particular property, namely that of "knock-down" in this instance.

EXAMPLE XII

| Flea and Tick Spray | |
|---|---|
| | PERCENT BY WEIGHT |
| Allethrin (90% technical) | 0.11% |
| Technical piperonyl butoxide | 1.0% |
| Butoxy Polypropylene Glycol | 5.0% |
| Cocodiethanolamide | 1.0% |
| Water | 92.89% |

This formulation fundamentally follows that for Example V set forth above, but eliminates the propellant as well as the butyl Cellosolve, with such constituents being replaced by water.

The foregoing examples demonstrate the broad range of insecticide active ingredients that may be incorporated, with special note being made of the fact that the same may be liquids, dry powders, and wettable powders. One example of the wettable powder is the carbamate insecticide identified by the trademark SEVIN (see page 21). It is understood that the dry powders must be rendered liquid and such is generally achieved by dissolving same in a compatible solvent. For instance, a typical solvent used in dissolution of chlorpyrofos is xylene, though experimentation has shown that other aromatic solvents and some chlorinated are compatible. However, the selection of a suitable solvent is within the scope of one having ordinary skill in the art but it is merely pointed out that in producing preparations of the present invention involving dry powders the same should be rendered liquid.

With respect to wettable powders it has been found that adding same into the water phase during production is desired. Otherwise, the actual methods for preparing insecticides according to the present invention follow generally established procedures, that is, firstly dissolving the same in some solvent, adding cocodiethanolamide in the prescribed amount thereby constituting the continuous phase, and then adding the water to this premixture with suitable agitation. With the insecticides in aerosol form, the ultimate dispensing container is then secured in accordance with present technology and with the intermixture of the active ingredient or continuous phase and the water phase being maintained in an agitated state to the point of filling. All of such steps are undertaken under ambient conditions so that there are no requirements for temperature, humidity, pressure, or other controls.

Upon compounding of the present inventions and with discontinuance of any agitation that may have been used for intermixing purposes, the water phase and the active ingredient or continuous phase will separate and remain in such independent states pending subsequent agitation immediately prior to dispensing or usage. It will be seen that such agitation prior to dispensing will bring about a transistory mixture of the two phases being, in essence, a rapid or most temporary dispersion in which state the discharge occurs. The shelf life of these preparations is most extensive since the cyclic mixing and separation as developed through use and non-use has no deleterious effect upon the ingredients and the phases so that regardless of the passage of time, the preparations will maintain their efficacy undiminished.

The foregoing examples, all of which are within the aforesaid neutral range of 6.5 to 7.5, show quite lucidly the singularly small amount of cocodiethanolamide required to promote the surprising and unexpected characteristics of these preparations. The amounts of cocodiethanolamide set forth in these examples are to be understood as the minimum amount required. As set forth above, the cocodiethanolamide may be within the range of 0.1 to 10% so that a compounder could theoretically increase the amount of cocodiethanolamide in the examples up to 10%. But if amounts were utilized in excess of that which was requisite, up to 10% by weight, it would, understandably, be necessary to add sufficient acidic agent to make certain that the neutral range was secured. It has been discovered that if amounts of cocodiethanolamide in excess of 10% were to be incorporated, the capacity of the cocodiethanolamide to assure a preparation of the properties sought for some reason, which is not altogether clear, is lost in that the preparations no longer exhibit the precise efficacious properties obtainable by utilization of cocodiethanolamide within the prescribed range. However, of exceeding importance is the fact that the present invention reveals that very limited amounts of cocodiethanolamide, as within the range of 0.1% to 2.4% with insecticidal preparations and air fresheners and if adjusted within the neutral range bring about results heretofore unknown.

Another class of preparations which may be made in accordance with the present invention are what are popularly referred to as aerosolized air fresheners, with such preparations, without enumeration, having an essential oil as the active ingredient. Thus, with these compounds one is concerned with fragrances which may be brought about by a single oil or blends of essential oils and would include synthetic fragrances and blends thereof as well as blends of essential oils and synthetic fragrances. Thus, these compounds provide the characteristic odor or flavor of a flower, fruit, plant, etc., and are fundamentally water insoluble. The same would not possess an inherent pH so that as utilized in systems of the type described hereinabove for insecticidal preparations, they would be subject to the pH provided by the cocodiethanolamide so that the latter could then be adjusted to the above-described neutral range.

It has been found that by utilizing cocodiethanolamide in aerosolized fragrance preparations, the relative quantity of propellant is markedly reduced from that which had been heretofore accepted, but without any diminution in effectiveness for deodorizing and like purposes.

The technology with respect to the formulation and production of aerosolized air fresheners or fragrance preparations follows the disclosure above with respect to propellants, auxiliary solvents, or film controllers, the incorporation of cocodiethanolamide within the same range, namely 0.1% to 10%, and with the preparation being within a pH of 6.7 to 7.5. The only distinction between these preparations and the insecticide preparations resides in the active ingredient, with all other components and proportionalities remaining compatibly the same.

The following is a general formulation for preparations of this type, namely - what has been referred to herein broadly as air fresheners, but which are, in fact, fragrance preparations with the same all being aerosolized and within the pH range of 6.5 to 7.5:

|  | PERCENT BY WEIGHT |
| --- | --- |
| Fragrance | q.s. |
| Solvent | Approx. 2.0% |
| Cocdiethanolamide | Approx. .1 to 10% |
| Propellant | Approx. 15.0% |
| Water | Approx. 50–83% |

The solvent utilized also acts to control particle size.

The following examples illustrate fragrance preparations in accordance with the present invention and indicate the substantially unlimited range of preparations which can be produced so that fragrances of any character can be easily presented.

EXAMPLE I

|  | PERCENT BY WEIGHT |
| --- | --- |
| Lemon Oil | 0.5% |
| Heptane | 2.0% |

-continued

| | PERCENT BY WEIGHT |
|---|---|
| Cocodiethanolamide | 0.3% |
| Water | 82.02% |
| (Isobutane 84%) | 15.0% |
| (Propane 16%) | |

The heptane, although acting as a solvent is used primarily to control particle size.

EXAMPLE II

| | PERCENT BY WEIGHT |
|---|---|
| Rose Fragrance | 0.25% |
| Ethanol | 2.00% |
| Cocodiethanolamide | 1.00% |
| Water | 81.75% |
| (Isobutane 84%) | 15.00% |
| (Propane 16%) | |

The ethanol serves to control particle size.

EXAMPLE III

| | PERCENT BY WEIGHT |
|---|---|
| Essential Oils | 11.25% |
| Isopar C* | 2.00% |
| Cocodiethanolamide | .50% |
| Water | 66.25% |
| (Isobutane 50%) | 20.00% |
| (Propane 50%) | |

This particular formulation is useful as a total release where there has been smoke damage.

EXAMPLE IV

| | PERCENT BY WEIGHT |
|---|---|
| Lavender Scent | 0.3% |
| Isopar L* | 2.5% |
| Cocodiethanolamide | 0.1% |
| Water | 82.0% |
| (Isobutane 65%) | 15.0% |
| (Propane 35%) | |

*A trademark of Humble Oil & Refining Co. for a group of high purity isoparaffinic material useful as odorless solvents

EXAMPLE V

| | PERCENT BY WEIGHT |
|---|---|
| Pine Fragrance | 1.0% |
| Odorless Mineral Spirits | 2.0% |
| Cocodiethanolamide | 0.6% |
| Water | 81.4% |
| (Isobutane 50%) | 15.0% |
| (Propane 50%) | |

These preparations may be produced by resort to customary procedures, such as, mixing the oil components, solvent and cocodiethanolamide with the water and then adjusting the system to the neutral range. Thereafter the mixture is properly introduced into a container and then provided with the selected propellant. Another method would be to add the acidic agent to the water in the necessary amount and then charge the water into a receptacle into which the mixture of the other phase containing the oil or oil blends, solvent, and cocodiethanolamide have already been introduced and thereafter adding the propellant. Consequently, the formation of fragrance preparations in accordance with this invention are easily and most economically effected, there being no unusual or novel techniques required.

What I claim is:

1. An insecticide preparation in the form of a dispersion comprising a water phase and an active ingredient phase which are normally separate, with distinct delineation between the same, said phases being capable of transitory intermixture upon agitation, there being a dispersal agent consisting of cocodiethanolamide in an amount within the range of 0.1 to 10% by weight of the preparation, said cocodiehanolamide being an amber liquid having a congealing point of approximately 6 degrees C., a specific gravity at 25 degrees C. of about 0.99, containing a maximum of about 3-4 percent free or unreacted fatty acid (as lauric acid) and having a pH value of 8-9 as a one percent dispersion in water, being soluble in alcohols, glycols, ketones, esters, aromatic and aliphatic hydrocarbons, and chlorinated solvents, and also being dispersible in water at low concentration of 1% to 2%, said active ingredient phase comprising an insecticidal agent selected from the class consisting of pyrethroids, carbamates, organo-phosphates, and combinations thereof in a quantity sufficient to exterminate the particular preselected prey, said dispersion having a pH within the range of approximately 6.5 to 7.5.

2. An insecticide preparation in the form of a dispersion as defined in claim 1 wherein the water content may constitute as much as 99.85% by weight of the preparation and the active ingredient may be within a range the lower limit of which is 0.05%.

3. An insecticided preparation in the form of a dispersion as defined in claim 2 wherein the active ingredient is water insoluble.

4. An insecticide preparation in the form of a dispersion as defined in claim 1 wherein the preparation is an aerosol containing a propellant from the class consisting of compressed gases, liquefied compressed gases and combinations of the same, there being a solvent compatible with said propellant.

5. An insecticide preparation in the form of a dispersion as defined in claim 1 wherein the preparation is an aerosol and comprises a propellant from the class consisting of liquefied hydrocarbons and halocarbons and combinations thereof, and being within a range of 2.5% to 30% by weight of the preparation, there being a solvent compatible with said propellant within the range of approximately 1% to 20% by weight of the preparation, and with the balance of said preparation being water.

6. An insecticide preparation in the form of a dispersion as defined in claim 1 wherein the preparation is an aerosol and comprises a compressed gas as a propellant and being within a range of 0.1% to 5% by weight of the preparation, there being a solvent compatible with said propellant within the range of approximately 0% to 20% by weight of the preparation, and with the balance of said preparation being water.

7. An insecticide preparation in the form of a dispersion as defined in claim 1 wherein the preparation is an aerosol and comprises a combination of a compressed gas or gases and liquefied compressed gas or gases as a propellant, with the liquefied compressed gas being within the range of 2% to 30% and the compressed gas being within the range of 0.1% to 5% by weight of the preparation, there being solvents compatible with the propellant, said solvents constituting approximately 1% to 20% by weight of the preparation, and with the balance of said preparation being water.

8. An insecticide preparation in the form of a dispersion as defined in claim 1 wherein the insecticidal agent is also from the class consisting of liquids and powders.

9. An insecticide preparation in the form of a dispersion as defined in claim 1 wherein the cocodiethanolamide has a solubility in each of said phases.

10. An insecticide preparation in the form of a dispersion as defined in claim 1, wherein the insecticidal agent is selected from the class consisting of neutral and synthetic pyrethroids and combinations thereof, said insecticide preparation further comprising a synergistic agent in combination with the selected pyrethroid or pyrethroids.

11. An insecticide preparation in the form of a dispersion as defined in claim 1 wherein the insecticidal agent is a carbamate and combinations thereof.

12. An insecticide preparation in the form of a dispersion as defined on claim 1 wherein the insecticidal agent is an organo-phosphate and combinations thereof.

* * * * *

UNITED STATES PATENT AND TRADEMARK OFFICE
CERTIFICATE OF CORRECTION

PATENT NO. : 4,904,464
DATED : February 27, 1990
INVENTOR(S) : James J. Albanese It is certified that error appears in the above-identified patent and that said Letters Patent is hereby corrected as shown below:

Column 16, Claim 3, line 35, "insecticided" should be "insecticide".

Column 18, Claim 10, line 1, "neutral" should be "natural".

Signed and Sealed this

Fifth Day of March, 1991

*Attest:*

HARRY F. MANBECK, JR.

*Attesting Officer*  *Commissioner of Patents and Trademarks*